United States Patent [19]

Yamamoto et al.

[11] Patent Number: 4,798,903
[45] Date of Patent: Jan. 17, 1989

[54] OPTICALLY ACTIVE 3,3'-DISILYLBINAPHTHOL DERIVATIVES

[75] Inventors: Hisashi Yamamoto, Aichi; Keiji Maruoka, Nagoya, both of Japan

[73] Assignee: Toyo Stauffer Chemical Co., Ltd., Tokyo, Japan

[21] Appl. No.: 160,258

[22] Filed: Feb. 25, 1988

[30] Foreign Application Priority Data

Mar. 10, 1987 [JP] Japan .................. 62-54857

[51] Int. Cl.⁴ .................................. C07F 7/08
[52] U.S. Cl. ........................................ 556/432
[58] Field of Search ............................ 556/432

[56] References Cited

U.S. PATENT DOCUMENTS

| | | | |
|---|---|---|---|
| 2,383,817 | 8/1945 | Rochow | 556/432 X |
| 3,137,720 | 6/1964 | Cooper | 556/432 |
| 3,464,937 | 9/1969 | Bamford et al. | 556/432 X |
| 3,576,021 | 4/1971 | Grindahl | 556/432 |
| 3,632,658 | 1/1972 | Halasa | 556/432 X |

*Primary Examiner*—Paul F. Shaver
*Attorney, Agent, or Firm*—Oblon, Fisher, Spivak, McClelland & Maier

[57] ABSTRACT

Optically active 3,3'-disilylbinaphthol derivatives are disclosed, which are represented by a general formula (I)

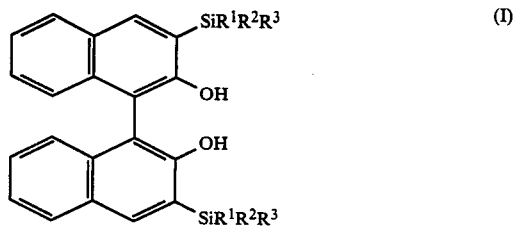

(wherein, $R^1$, $R^2$ and $R^3$ indicate mutually same or different lower alkyl groups and/or aromatic groups), and the steric configuration of which is R form or S form.

5 Claims, 3 Drawing Sheets

OPTICALLY ACTIVE 3,3'-DISILYLBINAPHTHOL DERIVATIVES

BACKGROUND OF THE INVENTION

The present invention relates to novel aptically active 3,3'-disilylbinaphthol derivatives.

No examples have ever been reported on the optically active 3,3'-disilylbinaphthol derivatives.

As a result of diligent studies, the inventor has found that the optically active 3,3'-disilylbinaphthol derivatives introduced the silyl group thereto are useful as ligands and, if using these, epoch-making catalysts for the reaction of asymmetric synthesis can be prepared, leading to the completion of the invention.

SUMMARY OF THE INVENTION

The gist of the invention lies in optically active 3,3'-disilylbinaphthol derivatives, which are represented by a general formula (I).

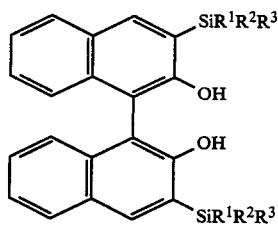
(I)

(wherein, $R^1$, $R^2$ and $R^3$ indicate mutually same or different lower alkyl groups and/or aromatic groups), and the steric configuration of which is R form or S form.

DETAILED DESCRIPTION OF THE INVENTION

Figure 1:
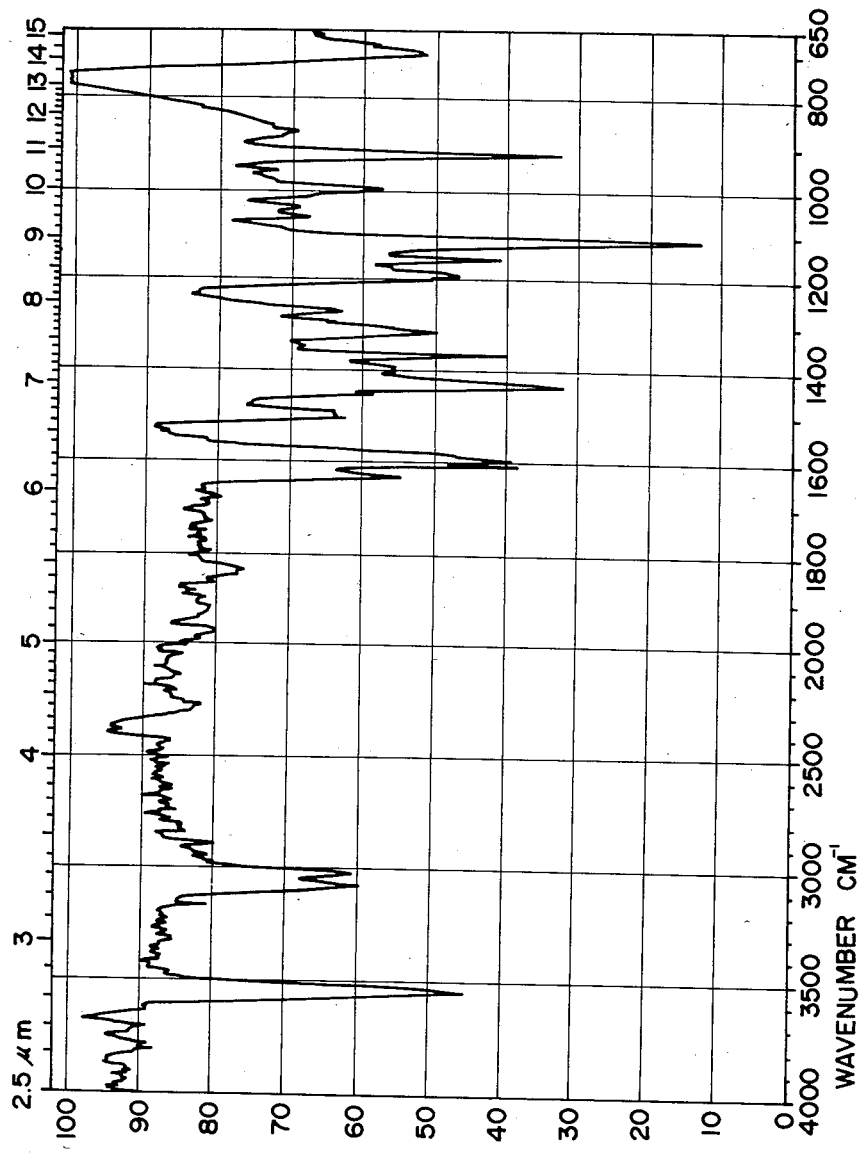
FIG. 1 through FIG. 3 are diagrams showing respectively IR spectra of the compounds relating to Example 1 through Example 3 of the invention.

In following, the invention will be illustrated in detail.

In the foregoing general formula (I), $R^1$, $R^2$ and $R^3$ are lower alkyl groups such as methyl, ethyl, n-propyl, i-propyl, n-butyl, sec-butyl, tert-butyl, n-pentyl, i-pentyl, neopentyl, n-hexyl, cyclohexyl, n-heptyl, n-octyl, i-octyl, etc. or aromatic groups such as phenyl, tolyl, benzyl, xylyl, i-butylphenyl, etc. These may be mutually same or different. Among these, methyl group, ethyl group, i-propyl group, sec-butyl group, tert-butyl group, neopentyl group, phenyl group and tolyl group are usually preferable.

If exemplifying some of optically active 3,3'-disilylbinaphthol derivatives relating to the invention. (R)-3,3'-bis(triethylsilyl)binaphthol, (S)-3,3'-bis(triethylsilyl)binaphthol, (R)-3,3'-bis(tert-butyldimethylsilyl)-binaphthol, (S)-3,3'-bis(tert-butyldimethylsilyl)binaphthol, (R)-3,3'-bis(triphenylsilyl)binapthol, (S)-3,3'-bis(triphenylsilyl)binaphthol, (R)-3,3'-bis(tert-butyldiphenylsilyl)-binaphthol, (S)-3,3'-bis(tert-butyldiphenylsilyl)binaphthol, etc. can be mentioned.

Said optically active 3,3'-disilylbinaphthol derivatives represented by the general formula (I) can be prepared as below.

Optically active 3,3'-dihalogenated binaphthol, which is represented by a general formula (II)

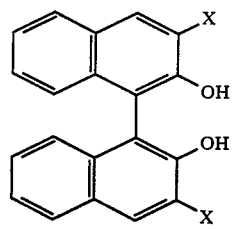
(II)

(wherein, X indicates a halogen atom),
and the steric configuration of which is R form or S form, is first allowed to react with halogenated tri-alkyl and/or -arylsilane represented by a general formula (III)

$$R^1R^2R^3SiX \qquad (III)$$

(wherein, $R^1$, $R^2$ and $R^3$ have same meaning as in general formula (I) and X indicates a halogen atom),
to produce optically active 3,3'-dihalogenated binaphthol bissilyl ether represented by a general formula (IV)

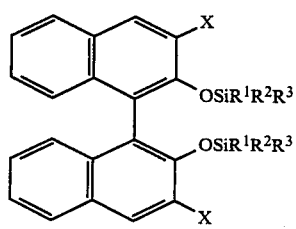
(IV)

(wherein, $R^1$, $R^2$ and $R^3$ have same meanings as in general formula (I) and X indicates a halogen atom).

By allowing this further to react with alkyllithium compound represented by a general formula (V)

$$R^4Li \qquad (V)$$

(wherein, $R^4$ indicates a lower alkyl group),
the preparation can be completed. As said X, chlorine or bromine is usually preferable. As $R^4$, sec-butyl group or tert-butyl group is usually used.

The optically active 3,3'-dihalogenated binaphthol represented by the general formula (II) can be synthesized by the method according to Cram et al (Journal of Organic Chemistry, 46, 393 (1981)). The reaction between this and halogenated tri-alkyl and/or -arylsilane represented by the general formula (III) is ordinarily conducted in an inert solvent and in the presence of a base.

As said inert solvent, dimethylformamide, dichloromethane or the like is preferable.

Moreover, as said base, amine such as imidazole, triethylamine, or the like is preferable.

The halogenated tri-alkyl and/or -arylsilane represented by the general formula (III) is used in amounts of 3 times mol or so, preferably 2 to 4 times mol, to optically active 3,3'-dihalogenated binaphthol represented by the general formula (II). Said inert solvent amounts about 0.2 to 10 liters to 1 mol of said optically active 3,3'-dihalogenated binaphthol.

Said base amounts 3 times mol or so, preferably 2 to 4 times mol, to 1 mol of said optically active 3,3'-dihalogenated binaphthol. The temperature of the reaction between said optically active 3,3'-dihalogenated binaphthol and said halogenated tri-alkyl and/or -arylsilane is usually −25° to 100° C., preferable 0° to 50° C. Moreover, the reaction time therefor is about 0.2 to 100 hours.

After the reaction, the optically active 3,3'-dihalogenated binaphthol bissilyl ether represented by the general formula (IV) can also be refined by combining appropriately, for example, filtration, washing, extraction, recrystallization, concentration, distillation, treatment with active charcoal, treatment with chromatograph, etc. according to the routine in organic chemistry.

The reaction between this optically active 3,3'-dihalogenated binaphthol bissilyl ether and alkyllithium compound represented by the general formual (V) is usually conducted in an inert solvent.

As said inert solvent, ethereal solvent such as tetrahydrofuran or the like is preferable.

Said alkyllithium compound is used in amounts of 3 times mol or so, preferably 2 to 4 times mol, to said optically active 3,3'-dihalogenated binaphthol bissilyl ether.

Said inert solvent amounts 0.2 to 10 liters to 1 mol of optically active 3,3'-dihalogenated binaphthol bissilyl ether. The temperature of the reaction between optically active 3,3'-dihalogenated binaphthol bissilyl ether and alkyllithium compound is ordinarily −80° to 100° C., preferably −20° C. to 50° C. Moreover, the reaction time therefor is about 0.1 to 100 hours.

After the reaction, the optically active 3,3'-disilylbinaphthol derivative can be refined by combining appropriately, for example, filtration, washing, extraction, recrystallization, concentration, distillation, treatment with active charcoal, treatment with chromatograph, etc. according to the routine in organic chemistry.

When allowing optically active 3,3'-disilylbinaphthol derivatives thus obtained to react with, for example, trialkylaluminum, optically active aluminum reagents in which two alkyl groups of aluminum are altered to optically active 3,3'-disilylbinaphthoxy groups can be obtained. These optically active aluminum reagents are useful as catalysts for the asymmetric hetero Diels-Alder reaction in the reactions between aldehydes and conjugated dienes to make it possible to obtain easily the optically active cyclic compounds. From this reason and others, the invention provides the compounds high in the usefulness as ligands of optically active catalysts.

In following the invention will be illustrated in more detail using examples, but it is not confined to following examples at any rate so long as the gist thereof is not exceeded.

EXAMPLE 1

Preparation of (R)-(+)-3,3'-bis(triphenylsilyl)binaphthol

Into a 200 ml three-neck flask equipped with a stirrer, dropping funnel and reflux condenser were charged 8.9 g (0.02 mol) of (R)-(+)-3,3'-dibromobinaphthol, and the inside of flask was substituted with nitrogen gas. Then, after added 100 ml of dimethylformamide, 5.4 g (0.08 mol) of imidazole were added and further 17.7 g (0.06 mol) of triphenylsilyl cholride were added little by little to produce dibromobinaphthol bis(triphenylsilyl) ether. After the completion of reaction, hydrolysis was made and thereafter the organic layer was extracted. The extracted liquor was dried and recrystallized to obtain 18.2 g (0.019 mol) of dibromobinaphthol bis(triphenylsilyl) ether. Into a 500 ml three-neck flask equipped with a stirrer, dropping funnel and reflux condenser were charged 18.2 g (0.019 mol) of dibromobinaphthol bis(triphenylsilyl) ether, and the inside of flask was substituted with nitrogen gas. Then, 20 ml of tetrahydrofuran were added and cooled to 0° C. Following this, the mixture was kept at 0° C. under stirring, while 65 ml (0.065 mol) of tert-butyllithium solution with a concentration of 1 mol/liter were added dropwise. After the completion of dropping, the temperature was returned to room temperature and the stirring was further continued for 2 hours. After completed the reaction, hydrolysis was maded and thereafter the organic layer was extracted. After dried and extracted liquor, solvent was distilled off. The residue was further submitted to silica gel chromatography and thereafter recrystallized to obtain 13.7 g (0.017 mol) of (R)-(+)-3,3'-bis(triphenylsilyl)binaphthol.

Elemental analysis:

|  | C | H |
|---|---|---|
| Theoretical (%) ($C_{56}H_{42}O_2Si_2$) | 83.75 | 5.27 |
| Observed (%) | 83.66 | 5.33 |

Specific rotation:
$[\alpha]_D^{25} = +124.65°$ (C=1.11, THF).

NMR Spectrum:

5.2 (2H, s, O—H), 6.93–7.87

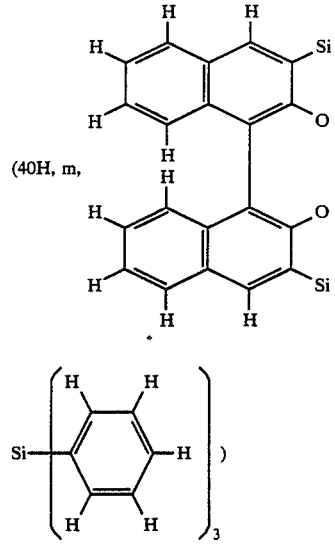

(40H, m,

IR Spectrum:
As FIG. 1.

EXAMPLE 2

Preparation of (R)-(+)-3,3'-bis(trimethylsilyl)binaphthol

Into a 200 ml three-neck flask equipped with a stirrer, dropping funnel and reflux condenser were charged 8.9 g (0.02 mol) of (R)-(+)-3,3'-dibromobinaphthol, and the inside of flask was substituted with nitrogen gas. Then, after added 100 ml of dichloromethane 5.4 g (0.08 mol) of triethylamine were added and further 6.5 g (0.06 mol) of trimethylsilyl chloride were added dropwise to produce dibromobinaphthol bis(trimethylsilyl) ether. After the completion of reaction, hydrolysis was made and thereafter the organic layer was extracted. The extracted liquor was dried to obtain 11.2 g (0.019 mol) of dibromobinaphthol bis(trimethylsilyl) ether. Into a 500 ml three-neck flask equipped with a stirrer, dropping funnel and reflux condenser were charged 11.2 g (0.019 mol) of crude dibromobinaphthol bis(trimethylsilyl) ether, and the inside of flask was substituted with nitrogen gas. Then, 200 ml of tetrahydrofuran were added and cooled to 0° C. Following this, the mixture was kept at 0° C. under stirring, while 65 ml (0.065 mol) of tert-butyllithium solution with a concentration of 1 mol/liter were added dropwise. After the completion of dropping, the temperature was returned to room temperature and the stirring was further continued for 2 hours. After completed the rection, hydrolysis was made and thereafter the organic layer was extracted. After dried the extracted liquor, solvent was distilled off. The residue was further submitted to silica gel chromatography and thereafter recrystallized to obtain 7.3 g (0.017 mol) of (R)-(+)-3,3'-bis(trimethylsilyl)binaphthol.

Elemental analysis:

|  | C | H |
| --- | --- | --- |
| Theoretical (%) ($C_{26}H_{30}O_2Si_2$) | 72.50 | 7.02 |
| Observed (%) | 72.62 | 7.12 |

Specific rotation:
$[\alpha]_D^{25} = +142.8°$ (C=0.985, THF).
NMR Spectrum:

0.39(18H, s, Si(CH$_3$)$_3$), 5.15(2H, s, O—H), 6.83-7.93(10H, m, 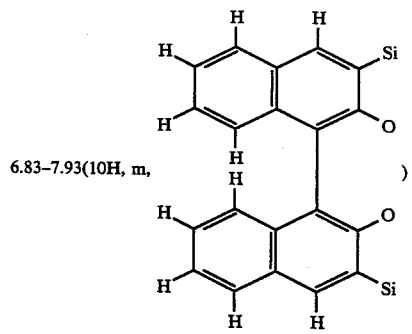 )

Figure 2:
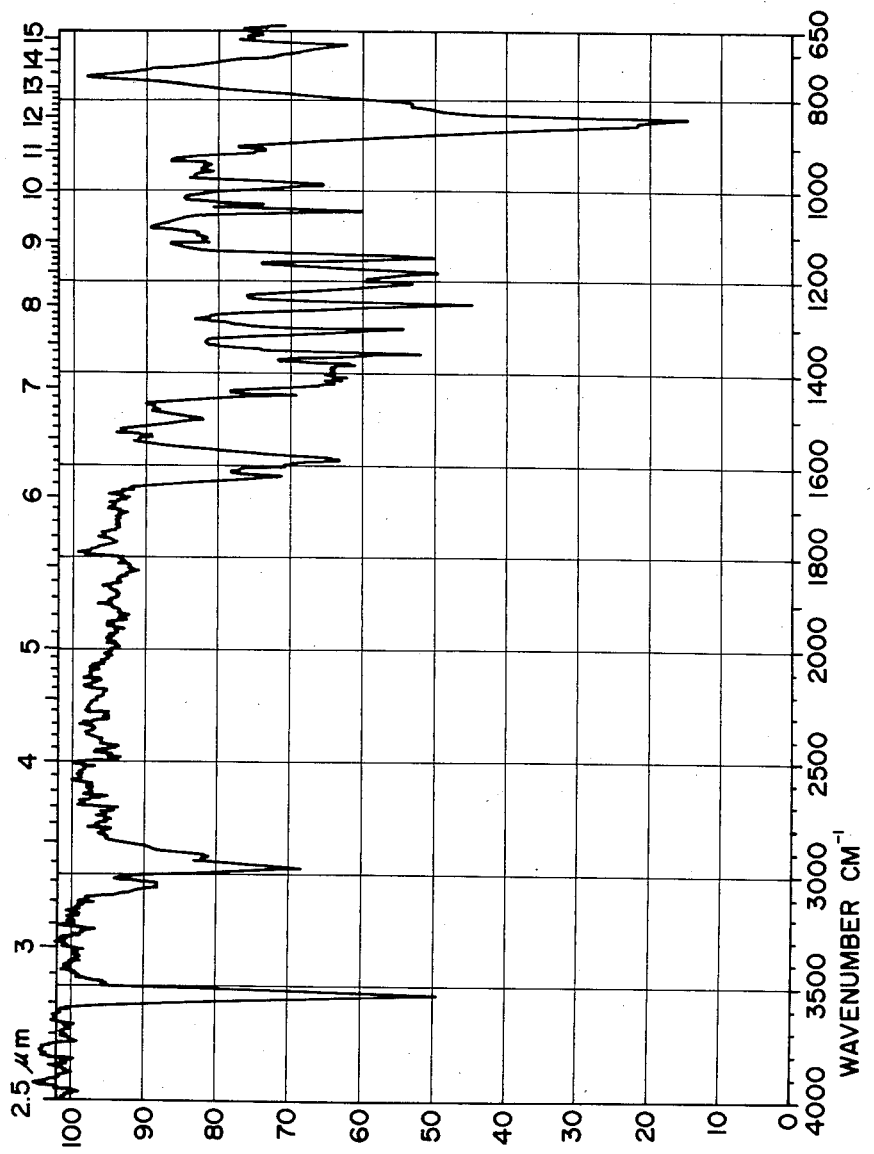

IR Spectrum:
As FIG. 2.

EXAMPLE 3

Preparation of
(R)-(+)-3,3'-bis(tert-butyldimethylsilyl)binaphthol

Into a 200 ml three-neck flask equipped with a stirrer, dropping funnel and reflux condenser were charged 8.9 g (0.02 mol) of (R)-(+)-3,3'-dibromobinaphthol, and the inside of flask was substituted with nitrogen gas. Then, after added 100 ml of dimethylformamide, 5.4 g (0.08 mol) of imidazole were added and further 9.0 g (0.06 mol) of tert-butyldimethylsilyl chloride were added dropwise to produce dibromobinaphthol bis(tert-butyldimethylsilyl) ether.

After the completion of reaction, hydrolysis was made and thereafter the organic layer was extracted. The extracted liquor was dried and recrystallized to obtain 12.8 g (0.019 mol) of dibromobinaphthol bis(tert-butyldimethylsilyl) ether. Into a 500 ml three-neck flask equipped with a stirrer, dropping funnel and reflux condenser were charged 12.8 g (0.019 mol) of dibromobinaphthol bis(tert-butyldimethylsilyl) ether, and the inside of flask was substituted with nitrogen gas. Then, 200 ml of tetrahydrofuran were added and cooled to 0° C. Following this, the mixture was kept at 0° C. under stirring, while 65 ml (0.065 mol) of tert-butyllithium solution with a concentration of 1 mol/liter were added dropwise. After the completion of dropping, the temperature was returned to room temperature and the stirring was further continued for 2 hours. After completed the reaction, hydrolysis was made and thereafter the organic layer was extracted. After dried the extracted liquor, solvent was distilled off. The residue was further submitted to silica gel chromatography and thereafter recrystallized to obtain 8.8 g (0.017 mol) of (R)-(+)-3,3'-bis(tert-butyldimethylsilyl)binaphthol.

Elemental analysis:

|  | C | H |
| --- | --- | --- |
| Theoretical (%) ($C_{32}H_{42}O_2Si_2$) | 74.65 | 8.22 |
| Observed (%) | 74.52 | 8.32 |

Specific rotation:
$[\alpha]_D^{25} = +136°$ (C=1.02, THF).
NMR spectrum:

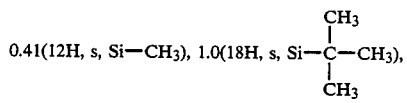

0.41(12H, s, Si—CH$_3$), 1.0(18H, s, Si—C(CH$_3$)$_3$), 5.07(2H, s, O—H), 6.80-7.90

(10H, m, 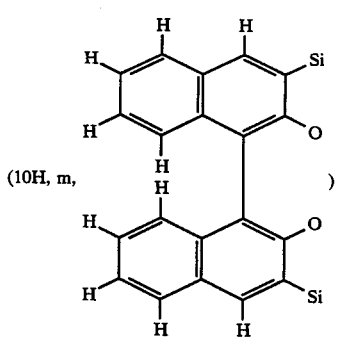 )

Figure 3:
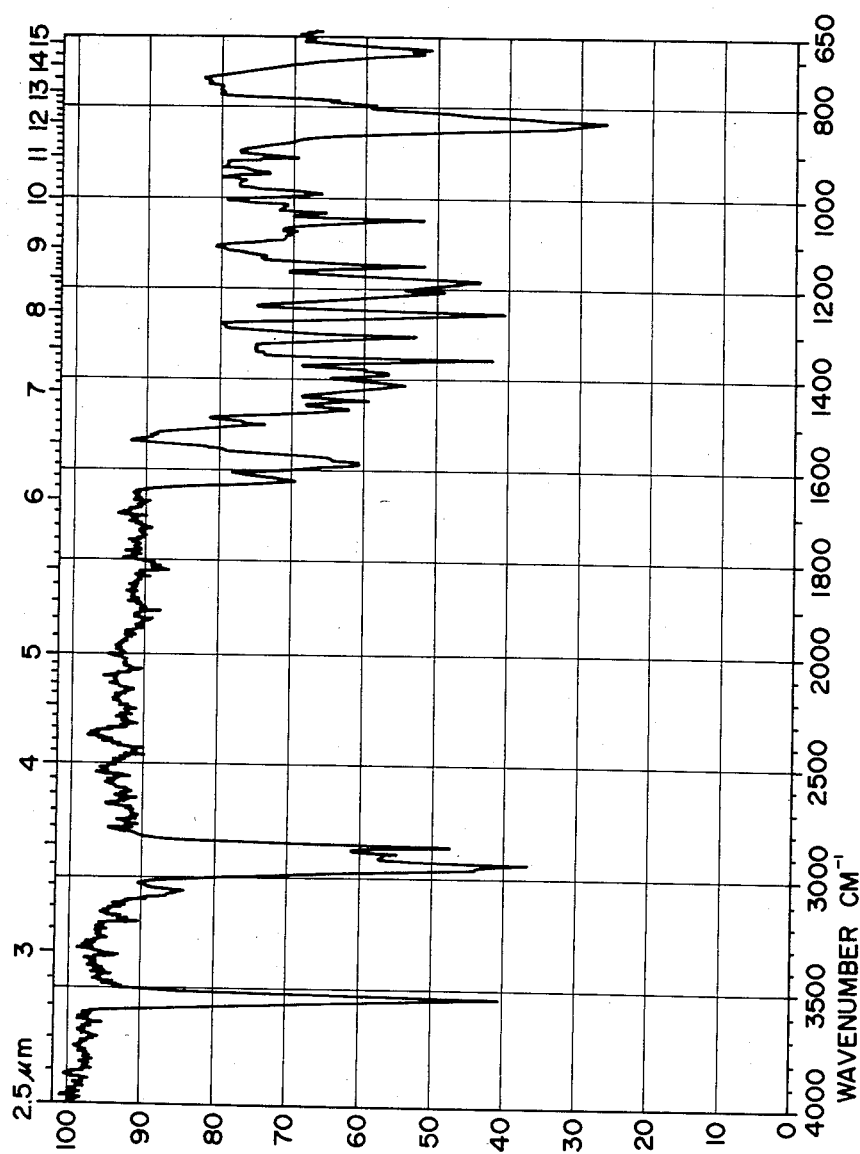

IR spectrum:
As FIG. 3.

The optically active 3,3'-disilylbinaphthol derivatives of the invention represented by the general formula (I) are novel compounds never found in the literatures and useful as ligands and as intermediates for the preparation of epoch-making catalysts for the asymmetric synthetic reaction.

What is claimed is:

1. Optically active 3,3'-disilylbinaphthol derivatives which are represented by a general formula (I)

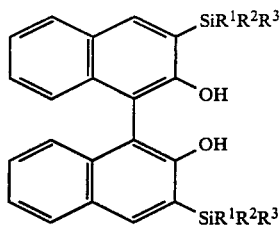

wherein $R^1$, $R^2$ and $R^3$ indicate mutually same or different lower alkyl groups and/or aromatic groups, and the steric configuration of which is R form or S form.

2. (R)-(+)-3,3'-bis(triphenylsilyl)binaphthol described in claim 1.

3. (R)-(+)-3,3'-bis(trimethylsilyl)binaphthol described in claim 1.

4. (R)-(+)-3,3'-bis(tert-butyldimethylsilyl)binaphthol described claim 1.

5. A method for preparing an optically active 3,3'-disilylbinaphthol derivative which is represented by a general formula (I)

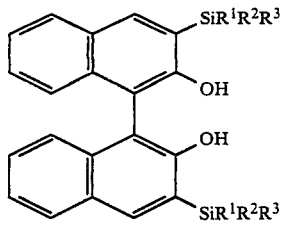

wherein $R^1$, $R^2$ and $R^3$ indicate mutually same or different lower alkyl groups and/or aromatic groups, characterized in that an optically active 3,3'-dihalogenated binaphthol bissilyl ether represented by a general formula (IV)

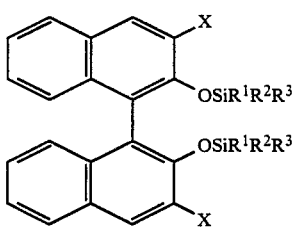

wherein $R^1$, $R^2$ and $R^3$ have the same meaning as above and X indicates a halogen atom is allowed to react with an alkyllithium compound represented by a general formula (V)

$$R^4Li \qquad (V)$$

wherein $R^4$ indicates a lower alkyl group.

* * * * *